United States Patent
Leal et al.

(10) Patent No.: US 9,957,211 B2
(45) Date of Patent: May 1, 2018

(54) METHODS AND SYSTEMS FOR SEPARATING C4 CRUDE STREAMS

(71) Applicant: SABIC GLOBAL TECHNOLOGIES B.V., Bergen op Zoom (NL)

(72) Inventors: Guillermo Leal, Riyadh (SA); Zeeshan Nawaz, Riyadh (SA); Renaat Hennus, Geleen (NL); Antonio Matarredona, Geleen (SA); Faisal Baksh, Manama (BH)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days. days.

(21) Appl. No.: 15/308,884

(22) PCT Filed: May 7, 2015

(86) PCT No.: PCT/IB2015/053354
§ 371 (c)(1),
(2) Date: Nov. 4, 2016

(87) PCT Pub. No.: WO2015/170282
PCT Pub. Date: Nov. 12, 2015

(65) Prior Publication Data
US 2017/0073289 A1    Mar. 16, 2017

Related U.S. Application Data

(60) Provisional application No. 61/989,602, filed on May 7, 2014.

(51) Int. Cl.
| | | |
|---|---|---|
| C07C 41/06 | (2006.01) | |
| C07C 7/167 | (2006.01) | |
| C07C 7/163 | (2006.01) | |
| C07C 7/13 | (2006.01) | |
| C07C 7/00 | (2006.01) | |
| C07C 7/04 | (2006.01) | |

(52) U.S. Cl.
CPC .............. *C07C 41/06* (2013.01); *C07C 7/005* (2013.01); *C07C 7/04* (2013.01); *C07C 7/13* (2013.01); *C07C 7/163* (2013.01); *C07C 7/167* (2013.01)

(58) Field of Classification Search
CPC ........... C07C 41/06; C07C 7/005; C07C 7/04; C07C 7/13; C07C 7/163; C07C 7/167; C07C 43/046; C07C 11/08; C07C 11/09
See application file for complete search history.

(56) References Cited

U.S. PATENT DOCUMENTS

| | | | |
|---|---|---|---|
| 2,859,173 A | 11/1958 | Hess et al. | |
| 2,882,243 A | 4/1959 | Milton | |
| 2,964,579 A | 12/1960 | Kirsch et al. | |
| 3,061,654 A | 10/1962 | Gensheimer et al. | |
| 3,076,858 A | 2/1963 | Frevel et al. | |
| 3,481,999 A | 12/1969 | Reich | |
| 4,493,906 A | 1/1985 | Couvillion | |
| 4,558,168 A * | 12/1985 | Gussow | C07C 11/08 568/697 |
| 4,587,369 A | 5/1986 | Cosyns et al. | |
| 4,704,492 A | 11/1987 | Nemet-Mavrodin | |
| 2010/0137664 A1 | 6/2010 | Lee et al. | |

FOREIGN PATENT DOCUMENTS

| | | |
|---|---|---|
| CA | 2264305 A1 | 9/1999 |
| DE | 111197 A1 | 2/1975 |
| WO | 8603484 A1 | 6/1986 |
| WO | 2012088245 A2 | 6/2012 |

OTHER PUBLICATIONS

Eastern Germany Patent No. 111197; Date of Publication: Oct. 1, 1986; Abstract Only, 1 page.
International Search Report for International Application No. PCT/IB2015/053354; dated Jul. 24, 2015; 5 pages.
Written Opinion of the International Search Report for International Application No. PCT/IB2015/053354; dated Jul. 24, 2015; 9 pages.
Adler, M.S. et al., "A Flexible Butylene Separation Process," Chemical Engineering Progress, 1979, pp. 77-79.

* cited by examiner

*Primary Examiner* — Rosalynd A Keys
(74) *Attorney, Agent, or Firm* — Cantor Colburn LLP

(57) ABSTRACT

The present invention provides, among other things, new processes for separating and purifying C4 fractions from a crude C4 stream. Compared to prior methods, the processes of the present invention simplify the C4 separation processes, afford more possible configurations for separation and purification, and are more cost effective. The processes and systems provided herein can be used as part of a cost-effective and efficient method for synthesizing methyl tertiary-butyl ether.

13 Claims, 5 Drawing Sheets

METHODS AND SYSTEMS FOR SEPARATING C4 CRUDE STREAMS

CROSS REFERENCE TO RELATED APPLICATIONS

This application is a 371 of International Application No. PCT/M2015/053354, filed May 7, 2015, which claims priority to U.S. Application No. 61/989,602, filed May 7, 2014 both which are incorporated herein by reference in their entirety.

FIELD OF THE INVENTION

The present invention relates to systems and methods for efficiently purifying and separating a crude C4 stream to extract components useful for synthesis of petrochemical products, thereby reducing operating costs and maximizing profit.

BACKGROUND OF THE INVENTION

Steam cracking hydrocarbons produces by-product fractions containing carbon compounds of various lengths. One valuable fraction is the C4 fraction, which typically contains linear C4 molecules (e.g., butane, 1-butene, 1,2-butadiene, and 1,3-butadiene), non-linear C4 molecules (e.g., isobutane and isobutene), and impurities. These impurities can include, for example, acetylinic impurities (e.g., vinylacetylene, methylacetylene) as well as residual hydrocarbons with five or more carbon atoms (sometimes referred to as "heavies"). When the C4 components are separated and purified, they find use as starting materials in the manufacture of a variety of petrochemical products. For example, isobutene that is obtained by purification of a crude C4 stream can be reacted with methanol to produce methyl tert-butyl ether (MTBE), an anti-knocking additive that is commonly added to gasoline.

Current methods employed to separate C4 fractions from a crude C4 stream demand significant capital investment. Therefore, it would be useful to have improved, more cost-effective processes for separating crude C4 streams into useful and purified C4 fractions.

SUMMARY OF THE INVENTION

Disclosed, in various embodiments, are methods for producing methyl tertiary-butyl ether.

A method of producing methyl tertiary-butyl ether, comprises: selectively hydrogenating a crude C4 stream to remove acetylinic impurities contained therein; distilling the hydrogenated crude C4 stream to remove butadiene impurities contained in the hydrogenated crude C4 stream, forming a distillate stream and a bottoms stream; exposing the distillate to a separation unit comprising a solid adsorbent to produce a first product stream comprising 1-butene and a second product stream comprising isobutene; reacting the second product stream with a methanol stream to produce methyl tertiary-butyl ether.

A method of producing methyl tertiary-butyl ether (MTBE), comprising: selectively hydrogenating a crude C4 stream to remove acetylinic impurities contained therein; distilling the hydrogenated crude C4 stream in a distillation unit to remove butadiene impurities contained in the hydrogenated crude C4 stream, forming a distillate stream and a bottoms stream; choosing a separation unit from either a first separation unit or a second separation unit, wherein the first separation unit and second separation unit are fluidly connected to the distillation unit and arranged in parallel; wherein the first separation unit comprises a first solid adsorbent capable of causing separation of the distillate stream into a first product stream comprising 1-butene and a first raffinate stream; and wherein the second separation unit comprises a second solid adsorbent different from the first solid adsorbent, the second solid adsorbent capable of causing separation of the distillate stream into a second product stream comprising a mixture of isobutene and isobutane and a second raffinate stream; exposing the distillate to the chosen separation unit to cause separation of the distillate such that, when the first separation unit is chosen, the first raffinate stream is reacted with a methanol stream to form methyl tertiary-butyl ether; and when the second separation unit is chosen, the second product stream is reacted with a methanol stream to form methyl tertiary-butyl ether.

A method of producing methyl tertiary-butyl ether, comprises: selectively hydrogenating a crude C4 stream to remove acetylinic impurities contained therein; distilling the hydrogenated crude C4 stream to remove butadiene impurities contained in the hydrogenated crude C4 stream, thereby forming a distillate stream and a bottoms stream; selectively hydrogenating the distillate stream to further reduce the concentration of butadiene impurities to form a first product stream; exposing the first product stream to a first separation unit comprising a solid adsorbent to produce a second product stream comprising 1-butene and a third product stream comprising a mixture of isobutene and isobutane; exposing the third product stream to a second separation unit comprising a solid adsorbent to produce a fourth product stream comprising a mixture of isobutene and isobutane and a fifth product stream enriched in 2-butenes; and reacting the fourth product stream with a methanol stream to produce methyl tertiary-butyl ether.

A method of producing methyl tertiary-butyl ether, comprises: selectively hydrogenating a crude C4 stream to remove acetylinic impurities contained therein; distilling the hydrogenated crude C4 stream to remove butadiene impurities contained in the hydrogenated crude C4 stream, thereby forming a distillate stream and a bottoms stream; selectively hydrogenating the distillate stream to further reduce the concentration of butadiene impurities to form a first product stream; exposing the first product stream to a first separation unit comprising a solid adsorbent to produce a second product stream comprising 1-butene and a third product stream comprising a mixture of isobutene and isobutane; exposing the second product stream to a second separation unit comprising a solid adsorbent to produce a fourth product stream comprising 1-butene and a fifth product stream comprising 2-butenes; and reacting the third product stream with a methanol stream to produce methyl tertiary-butyl ether.

A method of producing methyl tertiary-butyl ether, comprises: selectively hydrogenating a crude C4 stream to remove acetylinic impurities contained therein; distilling the hydrogenated crude C4 stream to remove butadiene impurities contained in the hydrogenated crude C4 stream, thereby forming a distillate stream and a bottoms stream; selectively hydrogenating the distillate stream to further reduce the concentration of butadiene impurities to form a first product stream; exposing the first product stream to a first separation unit comprising a solid adsorbent to produce a second product stream comprising 1-butene and a third product stream comprising a mixture of isobutene and isobutane; optionally exposing the third product stream a second separation unit to produce a fourth product stream comprising 2-butene and a fifth product stream comprising isobutene; reacting the fifth product stream with a methanol stream to produce methyl tertiary-butyl ether.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

DETAILED DESCRIPTION OF THE INVENTION

Figure 1:
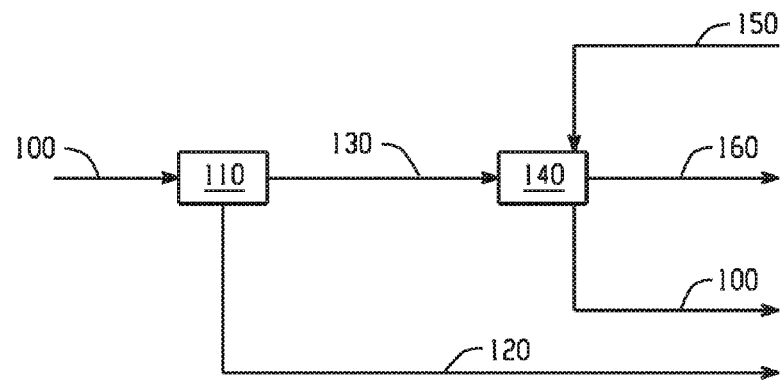
FIG. 1 is a schematic diagram depicting a general process for C4 processing in accordance with currently available systems and methods.

This invention provides novel methods and systems for purifying and separating crude C4 streams to produce C4 streams suitable for use as an input stream for the synthesis of MTBE or other valuable petrochemical products. In comparison to current methods and systems, the invention described herein offers lower cost, more efficient, and more flexible methods for purifying and separating C4 streams into its useful components such as 1-butene, 2-butenes, isobutene, and the like.

The present invention provides, among other things, new processes and systems for separating and purifying C4 fractions from a crude C4 stream. Compared to prior methods, the processes of the present invention simplify the C4 separation processes, afford more possible configurations for separation and purification, and are more cost effective. The processes and systems provided herein can be used as part of a cost-effective and efficient method for synthesizing MTBE. For example, using the methods and systems disclosed herein, it is possible to achieve a 20-30% increase in MTBE production, even with just a modest increase (e.g., 10%) in the physical flow of feedstock streams.

In one aspect, the invention provides a method of producing methyl tertiary-butyl ether that includes selectively hydrogenating a crude C4 stream to remove acetylinic impurities contained in the crude C4 stream. The hydrogenated crude C4 stream is then distilled to remove butadiene impurities contained in the hydrogenated crude C4 stream, thereby forming a distillate stream and a bottoms stream. The distillate is exposed to a separation unit comprising a solid adsorbent (e.g., molecular sieves) to produce a first product stream that comprises predominantly 1-butene and a second product stream that comprises isobutene. The second product stream is reacted with a methanol stream to produce MTBE. If desired, the method can include an additional step whereby the distillate is selectively hydrogenated to substantially reduce the concentration of butadiene impurities prior to exposing the distillate to the separation unit.

In another aspect, the invention provides a method of producing methyl tertiary-butyl ether that includes selectively hydrogenating a crude C4 stream to remove acetylinic impurities. The hydrogenated crude C4 stream is distilled in a distillation unit to remove butadiene impurities contained in the hydrogenated crude C4 stream, forming a distillate stream and a bottoms stream. The distillate stream is then sent to a first separation unit or a second separation unit for further separation, wherein the chosen separation unit will depend on the desired process and/or products. The first separation unit and the second separation are both fluidly connected to the distillation unit and are arranged in parallel. The first separation unit comprises a first solid adsorbent capable of causing separation of the distillate stream into a first product stream comprising predominantly 1-butene and a first raffinate stream. The second separation unit comprises a second solid adsorbent that is different from the first solid adsorbent. The second solid adsorbent is capable of causing separation of the distillate stream into a second product stream comprising predominantly a mixture of isobutene and isobutane and a second raffinate stream. When the first separation unit is chosen, the first raffinate stream is reacted with a methanol stream to form MTBE. When the second separation unit is chosen, the second product stream is reacted with a methanol stream to form MTBE.

In yet another aspect, the invention provides a method of producing methyl tertiary butyl ether that includes selectively hydrogenating a crude C4 stream to remove acetylinic impurities contained in the crude C4 stream. The hydrogenated crude C4 stream is then distilled to remove butadiene impurities, thereby forming a distillate stream and a bottoms stream. The distillate stream is then selectively hydrogenated to further reduce the concentration of butadiene impurities, thereby forming a first product stream. This first product stream is exposed to a first separation unit comprising a solid adsorbent to produce a second product stream comprising predominantly 1-butene and a third product stream comprising a mixture of isobutene and isobutane. The third product stream is exposed to a second separation unit comprising a solid adsorbent to produce a fourth product stream comprising a mixture of isobutene and isobutane and a fifth product stream enriched in 2-butenes. The fourth product stream reacts with a methanol stream to produce MTBE.

The invention also provides a method of producing MTBE that includes selectively hydrogenating a crude C4 stream to remove acetylinic impurities and then distilling the hydrogenated crude C4 stream to remove butadiene impurities, thereby producing a distillate stream and a bottoms stream. The distillate stream is selectively hydrogenated to further reduce the concentration of butadiene impurities to form a first product stream. The first product stream is exposed to a first separation unit comprising a solid adsorbent to produce a second product stream comprising predominantly 1-butene and a third product stream comprising predominantly a mixture of isobutene and isobutane. The second product stream is exposed to a second separation unit comprising a solid adsorbent to produce a fourth product stream comprising predominantly 1-butene and a fifth product stream comprising predominantly 2-butenes. The third product stream is reacted with a methanol stream to produce MTBE.

The invention also provides a method of producing MTBE that includes selectively hydrogenating a crude C4 stream to remove acetylinic impurities and distilling the hydrogenated crude C4 stream to remove butadiene impurities, thereby forming a distillate stream and a bottoms stream. The distillate stream is selectively hydrogenated to further reduce the concentration of butadiene impurities to form a first product stream. The first product stream is exposed to a first separation unit comprising a solid adsorbent to produce a second product stream comprising predominantly 1-butene and a third product stream comprising a mixture of isobutene and isobutane. Optionally, the third product stream is exposed to a second separation unit to produce a fourth product stream comprising predominantly 2-butene and a fifth product stream comprising predominantly isobutene. The fifth product stream is reacted with a methanol stream to produce MTBE FIG. 1 depicts a conventional process for synthesizing MTBE. C4 olefin stream 100, which can contain a mixture of C4 olefins (e.g., one or more of butadiene, isobutene, 1-butene and the two 2-butenes), acetylinic impurities, and C4 alkanes (e.g., isobutane and/or n-butane), are sent to a butadiene extraction unit 110 to remove butadiene impurities from olefin stream 100. The butadiene impurities are removed as stream 120 and raffinate stream 130 is combined with methanol stream 150 in a reactor 140, where they react to form MTBE. Typically, the reaction is performed over a catalyst, a non-limiting example of which is an acid exchange catalyst. The MTBE is recovered as stream 100 and raffinate stream 160 is optionally sent to downstream processing unit, where further separation and/or purification can occur.

FIGS. 2 to 7 are flow diagrams that schematically depict C4 separation and purification methods and systems in accordance with exemplary implementations of the invention. In preferred embodiments of the invention, the crude C4 stream to be purified and separated is first selectively hydrogenated to remove acetylinic impurities that can be present. These acetylinic impurities (which can include, for example, vinylacetylene, methylacetylene and/or ethylacetylene) are typically generated as by-products during upstream hydrocracking processes that produce the crude C4 stream. The presence of such acetylinic impurities is considered to be undesirable, because they can result in detonation when they are present at sufficiently high concentration (see, e.g., WO 2012088245 A2). As shown in FIGS. 2-7, a crude C4 stream 200, 300, 400, 500, 600, or 700, respectively, is subjected first to a selective hydrogenation step in a hydrogenation reactor, which is depicted as 210, 310, 410, 510, 610, or 710 in FIGS. 2-7, respectively. In certain embodiments, the concentration of residual acetylinic impurities after the selective hydrogenation step is 0.0001 to 0.5 weight percent (wt. %), 0.0005 to 0.4 wt. %, 0.001 to 0.3 wt. % or 0.05 to 0.2 wt. %. Preferably, the concentration of residual acetylinic impurities after the selective hydrogenation step is less than 100 parts per million (ppm), 90 ppm, 80 ppm, 70 ppm, 50 ppm, or 40 ppm. The selective hydrogenation of the acetylinic impurities can be carried out by processes generally known in the art. Such processes include, for example, selective hydrogenation over supported metal catalysts as disclosed in U.S. Pat. Nos. 4,587,369; 4,493,906; and 4,704,492. If desired, palladium/alumina catalysts or copper/gamma alumina catalysts can be used, as reported, for example, in U.S. Pat. No. 4,704,492. These references, as well as all others cited herein, are expressly incorporated reference in their entirety, unless otherwise noted.

As the skilled artisan will appreciate, the specific operating conditions (e.g., flow rates, pressures, temperatures, etc.) will depend on a variety of factors, including the catalysts chosen and the compositions of the C4 streams to be selectively hydrogenated. With this in mind, selective hydrogenation is typically run at an operating pressure of 20-40 bar, 25-40 bar, or 30-35 bar. Operating temperatures can be 15-75° C., 20-70° C., 25-65° C., 30-60° C. To achieve the desired concentration of acetylinic impurities, the invention contemplates using one or more hydrogenation reactors to selectively hydrogenate the crude C4 stream. In one preferred embodiment, two hydrogenation reactors are used in series to selectively hydrogenate the crude C4 stream.

Preferably, the selectively hydrogenated C4 stream is then distilled to remove heavy impurities (e.g., impurities containing five or more carbon atoms, sometimes referred to as "heavies"), as well as butadienes, which can include 1,3-butadiene and/or 1,2-butadiene. One aspect of the invention is the recognition that a distillation column can be used to obtain distillate butene streams that have low amounts of butadiene impurities, 2-butene or heavies, thus reducing the vapor load to other downstream separation units. This distillation step can be accomplished, for example, by passing the selectively hydrogenated crude C4 stream through one or more extractive distillation columns (EDCs). EDCs are known in the art (see, e.g., U.S. Patent Publication No. 2010/0137664). This is illustrated, for example, in FIGS. 2-7, where selectively hydrogenated C4 streams 220, 320, 420, 520, 620, or 720 are passed through corresponding distillation columns 230, 330, 430, 530, 630, and 730. In some embodiments, the concentration of butadienes in the crude C4 stream, prior to distillation, is typically 25-60 wt %. In preferred embodiments, the distillation step reduces the concentration of butadienes in the C4 stream to less than 20 wt. %, 15 wt. %, 10 wt. %, or 5 wt. %. For example, the concentration of butadienes in the distillate obtained from the distillation step can be 5-20 wt. %, more preferably 5-15 wt. %, even more preferably 5-10%. In certain embodiments, the concentration of butadienes in the distillate is approximately 7.5%. With respect to separating 1-butene from isobutene, the invention recognizes that the boiling points of 1-butene and isobutene differ by less than 1° C., and so distillation is not a practical method to achieve separation of these species. Accordingly, upon removal of the butadiene impurities, the distillates 230a, 330a, 430a, 530a, 630a, and 730a are further subjected to processes as disclosed below.

Figure 2:
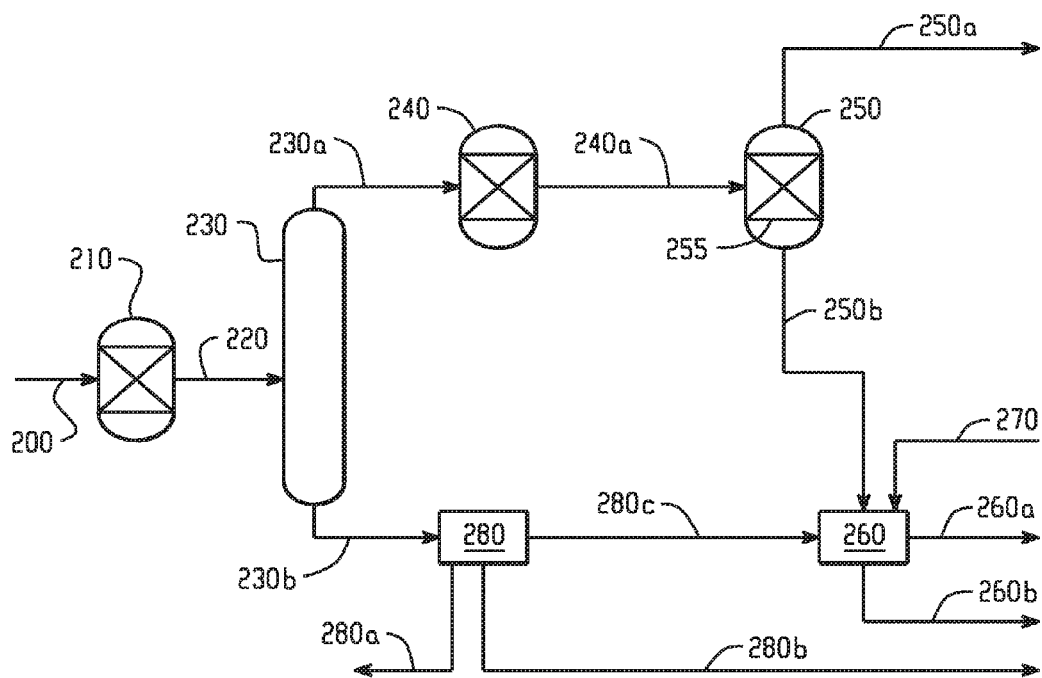
FIG. 2 is a schematic diagram depicting a method for C4 purification for MTBE synthesis in accordance with an exemplary implementation of the present disclosure.

FIG. 2 is a flow chart that schematically depicts an exemplary method and system for separating and purifying a C4 stream according to one implementation of the invention. Distillate 230a (which is produced in accordance with the process described above) preferably contains approximately 30 wt. % 1-butene, approximately 50% of a mixture of isobutene/isobutane and 5-10 wt. % of butadiene impurities. Distillate 230a is preferably exposed to second selective hydrogenation unit 240 to further remove butadiene impurities, thereby producing distillate stream 240a. In this embodiment and others disclosed herein, selective hydrogenation to remove butadiene impurities can be achieved by methods known in the art. For example, selective hydrogenation of butadienes can be achieved by using copper chromite catalysts (U.S. Pat. No. 2,964,579), copper catalysts which contain 0.1 to 0.001% of Pd, Ru, Fe, Ni, Rh, Ir or Pt (see, e.g., U.S. Pat. No. 3,076,858, which is incorporated by reference in its entirety), or copper catalysts with "modifiers" such as chromium, chromium oxide, phosphate or magnesium (see, e.g., U.S. Pat. No. 3,481,999, which is also incorporated by reference in its entirety). When copper catalysts with such modifiers are used, the modifiers are preferably present in quantities of from 0.05 to 15 wt. %, preferably 0.2 to 3 wt. %.

Distillate stream 240a then sent to separation unit 250, which comprises solid adsorbents, such as, for example molecular sieves (illustrated in FIG. 2 by reference numeral 255). Molecular sieves are crystalline zeolite materials that have pore openings of uniform size that permit adsorption of molecules having cross sectional areas equal or smaller than the pore opening but reject molecules with larger diameters. Molecular sieves can be naturally occurring (e.g., chabazite and analcite) or synthetically produced (see, e.g., U.S. Pat. No. 2,882,243). In certain preferred embodiments, the molecular sieves are selected such that their pore sizes permit preferential passage of certain types molecules in the C4 stream over other types. For example, in certain embodiments, the molecular sieves are chosen for their ability to adsorb straight chain hydrocarbons while excluding branched hydrocarbons (e.g., isobutene). By way of example, chabazite exhibits such desirable properties. Another suitable natural zeolite is analcite, a sodium aluminosilicate, will adsorb straight chain hydrocarbons while substantially excluding branched hydrocarbons. See, e.g., U.S. Pat. Nos. 2,859,173 and 3,061,654. The classes of materials that can be used to fabricate the solid adsorbents contemplated by the invention include silicates, aluminosilicates, aluminophosphates, and silicoaluminophosphates, to name a just a few. In certain embodiments, the molecular sieves are metal impregnated/alkali exchanged zeolites, non-limiting examples of which include 3 A, 4 A, 5 A, and 13×. By using molecular sieves as taught herein, one can generate highly pure 1-butene streams (e.g., about 99 wt. % 1-butene).

In FIG. 2, separation unit 250 separates distillate 240a-into product streams 250a and 250b. Preferably, the molecular sieves 255 present in separation unit 250 are chosen such that product stream 250a comprises predominantly 1-butene, preferably at a concentration of greater than 90 wt. %. For example, the concentration of 1-butene in product stream 250a can be at least 95%, and in certain embodiments is 96, 97, 98, or 99 wt. %. Product stream 250b comprises chemical species from the remaining fraction of distillate 240a and includes branched C4 molecules (e.g., isobutene, isobutane), as well as 2-butenes. As indicated in FIG. 2, this embodiment of the invention contemplates directly using product stream 250b as an input stream to MTBE synthesis reactor 260. FIG. 2 shows two other input streams into reactor 260, namely methanol stream 270 and raffinate stream 280c, which is enriched in isobutene and produced by treating bottoms stream 230b (formed by distillation unit 230) with an additional butadiene removal unit 280. The MTBE that is produced by MTBE synthesis unit 260 is recovered as product stream 260b, while other components, such as 1-butene and 2-butenes, are recovered as raffinate stream 260a. FIG. 2 also shows that butadiene removal unit 280 produces butadiene stream 280a, as well as raffinate stream 280b, both of which can be subjected to further downstream processing, if desired.

Figure 3:
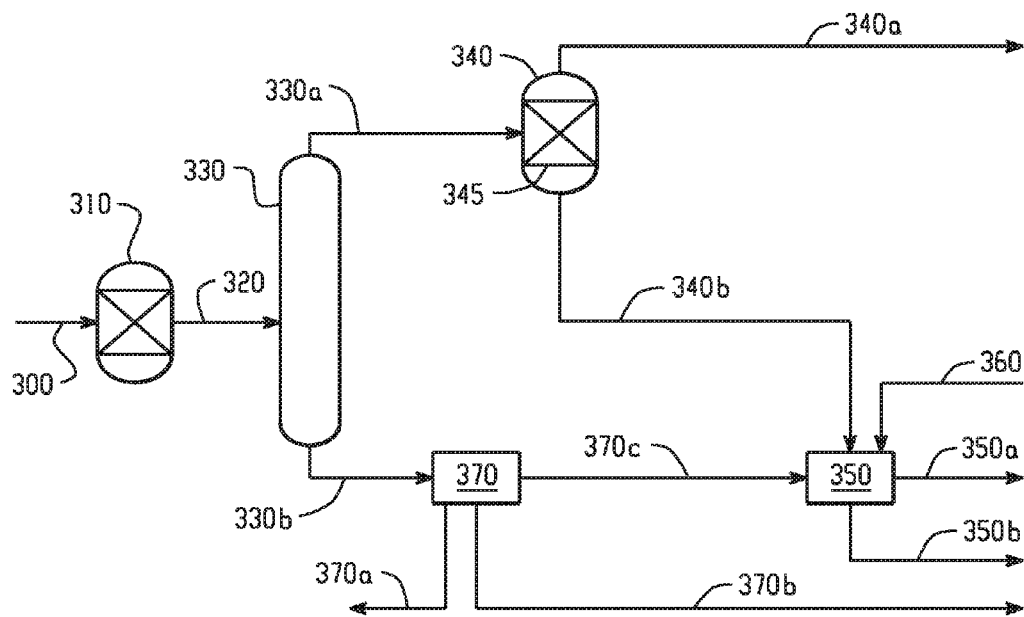
FIG. 3 is a schematic diagram depicting a method for C4 purification for MTBE synthesis in accordance with an exemplary implementation of the present disclosure.

FIG. 3 is a flow chart that schematically depicts an exemplary method and system for separating and purifying a C4 stream according to another implementation of the invention. Distillate 330a from distillation unit 330 is sent to separation unit 340 comprising molecular sieves 345, which are useful for separating 1-butene from the remaining components of distillate 330a. Preferably, molecular sieves 345 are synthetic zeolites (crystalline metal aluminosilicates) which upon dehydration can efficiently and selectively remove water or other solvents. The selectivity of a molecular sieve is determined by its pore size, and molecules with a critical diameter which is less than the pore size will be efficiently adsorbed while larger molecules will be excluded. In certain preferred embodiments, the molecular sieves are metal impregnated/alkali exchanged zeolites as discussed above. Non-limiting examples of molecular sieves that are suitable for achieving this separation include molecular sieves with 3 Å, 4 Å, 5 Å, or 10 Å (13×) pore sizes. Separation unit 340 separates branched C4 molecules (isobutene and isobutene) from distillate 330a to form product streams 340a and 340b. Raffinate product stream 340a comprises a mixture of hydrocarbons, but in preferred embodiments comprises predominantly 1-butene. In certain embodiments, the concentration of 1-butene in product stream 340b is 50-70 wt. % 1-butene, and more preferably 60-70 wt. % 1-butene. Product stream 340b is enriched in iC4's (isobutene and isobutane) and can be directly used as an input stream for MTBE synthesis unit 350. In certain embodiments, the iC4 species are present in product stream 340b at a concentration of at least 80 wt. %, 85 wt. % 90% wt. %, or 95 wt. %.

FIG. 3 shows two other input streams into MTBE synthesis unit 350, namely methanol stream 360 and raffinate stream 370c, which is enriched in isobutene and produced by treating bottoms stream 330b (formed by distillation unit 330) with an additional butadiene removal unit 370. The MTBE that is produced by MTBE synthesis unit 350 is recovered as product stream 350b, while other components, such as 1-butene and 2-butenes, are recovered as raffinate stream 350a. FIG. 3 also shows that butadiene removal unit 370 produces butadiene stream 370b, as well as raffinate stream 370a.

Figure 4:
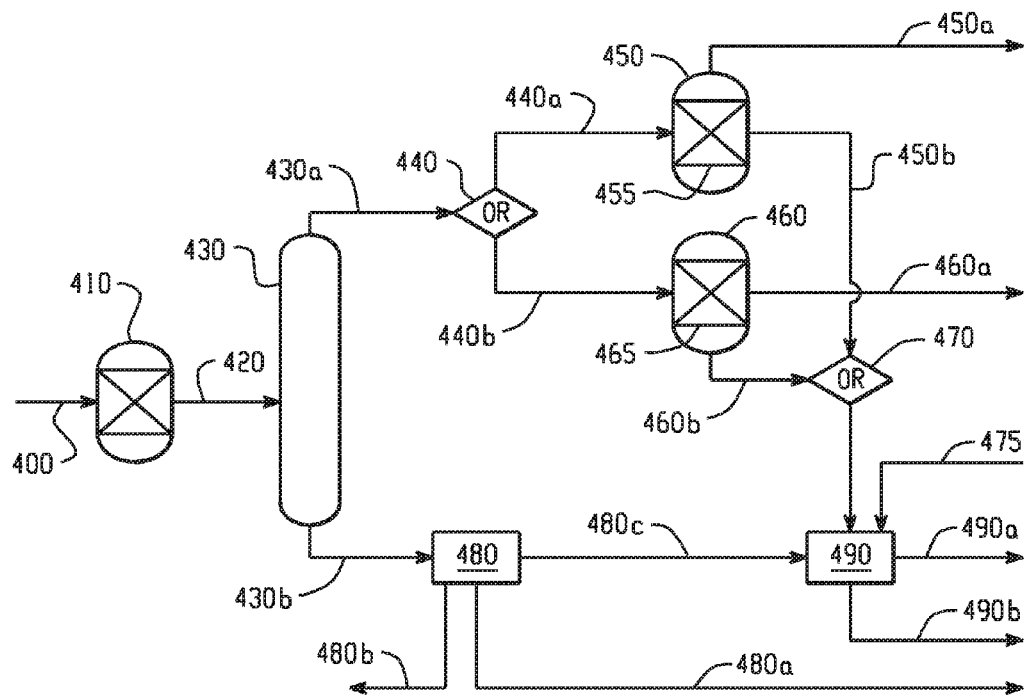
FIG. 4 is a schematic diagram depicting a method for C4 purification for MTBE synthesis in accordance with another exemplary implementation of the present disclosure.

FIG. 4 schematically depicts an exemplary method and system for separating and purifying a C4 stream according to yet another implementation of the invention. Distillate 430a from distillation unit 430a is sent to either 1-butene separation unit 450 or iC4 separation unit 460 via a 3-way diverter valve 440 where stream 440a diverts distillate 430a to 1-butene separation unit 450 and stream 440b diverts distillate 430a to iC4 separation unit 460. Such valves are commercially available (e.g., from MOGAS Industries, Inc., Houston, Tex.) and well known in the art. The 1-butene separation unit 450 comprises molecular sieves 455, which preferably are crystalline aluminosilicates and are useful for separating 1-butene from the remaining species in distillate 430a. When distillate 430a is sent to 1-butene separation unit 450, the separation results in product streams 450a and 450b. In preferred embodiments, product stream 450a is highly enriched in 1-butene and can have a 1-butene concentration of at least 90 wt. %, preferably 93 wt. %, even more preferably 96%, and most preferably 99 wt. %. Product stream 450b, which is a raffinate stream that contains isobutene, can be used as an input stream for MTBE synthesis unit 490. The iC4 separation unit 460 comprises molecular sieves 465, which can be used to separate 1-butene from the remaining species in distillate 430*a*. The molecular sieves 465 preferably are microporous material which can selectively adsorb gases and liquids as described herein. When distillate 430*a* is sent to iC4 separation unit 460, the separation results in product stream 460*b*, which is highly enriched in isobutene and isobutane and suitable for use as an input stream for MTBE synthesis unit 490. Corresponding raffinate stream 460*a* is diverted for other uses, and can be subjected to further subsequent downstream processing. A 3-way valve 470 can be used to select which of product streams 450*b* and 460*b* are used as an input stream for MTBE synthesis unit 490. FIG. 4 shows two other input streams into MTBE synthesis unit 490, namely methanol stream 475 and raffinate stream 480*c*, which is enriched in isobutene and produced by treating bottoms stream 430*b* (formed by distillation unit 430) with an additional butadiene removal unit 480. The MTBE that is produced by MTBE synthesis unit 490 is recovered as product stream 490*b*, while other components, such as 1-butene and 2-butenes, are recovered as raffinate stream 490*a*. FIG. 4 also shows that butadiene removal unit 480 produces butadiene stream 480*a*, as well as raffinate stream 480*b*.

Figure 5:
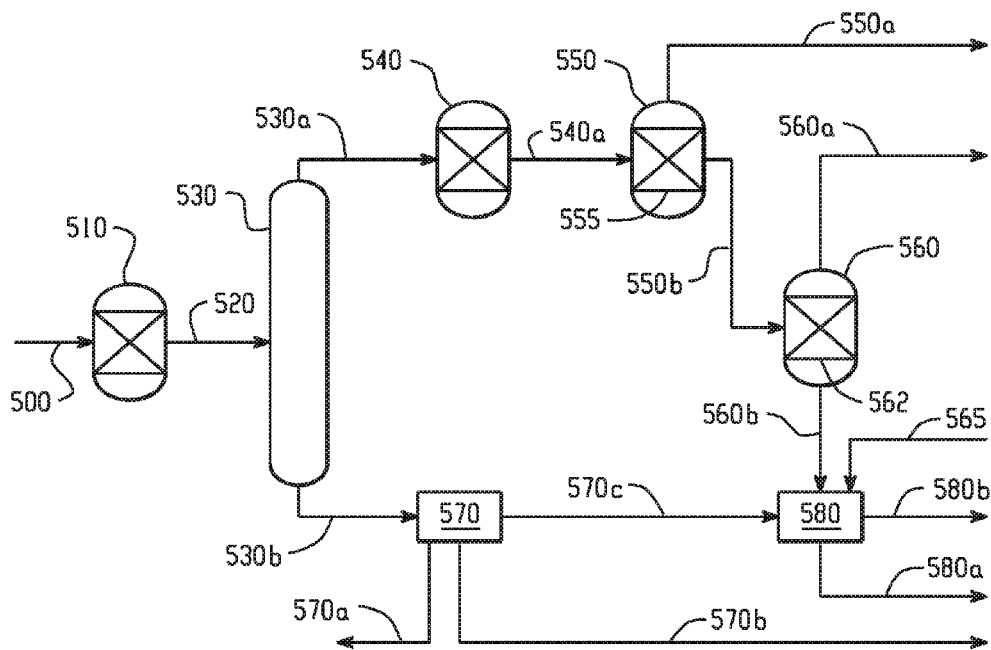
FIG. 5 is a schematic diagram depicting a method for C4 purification for MTBE synthesis in accordance with another exemplary implementation of the present disclosure.

FIG. 5 schematically depicts an exemplary method and system for separating and purifying a C4 stream according to yet another implementation of the invention. Distillate 530*a* from distillation unit 530 is sent to selective hydrogenation unit 540 to reduce the concentration of butadiene impurities. In certain embodiments, distillate 530*a* (which is produced in accordance with the process described above) can contain approximately 30 wt. % 1-butene, approximately 50% of a mixture of isobutene/isobutene and 5-10 wt. % of butadiene impurities. Distillate 530*a* is preferably exposed to second selective hydrogenation unit 540 to remove butadiene impurities, thereby producing distillate stream 540*a*. This distillate stream is then sent to separation unit 550, which comprises solid adsorbents, such as, for example molecular sieves (illustrated in FIG. 5 by reference numeral 555). Preferably, the molecular sieves 555 present in separation unit 550 are chosen such that product stream 550*a* comprises predominantly 1-butene, which is present in some embodiments at a concentration of greater than 90 wt. %. For example, the concentration of 1-butene in product stream 550*a* can be at least 95%, and in certain embodiments is 96, 97, 98, or 99 wt. %. Non-limiting examples of molecular sieves that are suitable for achieving this separation include those described herein, e.g., molecular sieves with 3 Å, 4 Å, 5 Å, or 10 Å (13×) pore sizes. Product stream 550*b* comprises chemical species from the remaining fraction of product stream 540*a* and includes branched C4 molecules (e.g., isobutene, isobutane), as well as 2-butenes. As shown in FIG. 5, product stream 550*b* serves as an input stream for iC4 separation unit 560, which comprises molecular sieves 562. Separation unit 560 separates product stream 550*b* into iC4 stream 560*b* and raffinate stream 560*a*. Product stream 560*b* is used as an input stream for MTBE synthesis unit 580, while raffinate stream 560*a* (which is enriched in 2-butenes) is directed to other uses, and can be subjected to subsequent downstream processing. FIG. 5 shows two other input streams into MTBE synthesis unit 580, namely methanol stream 565 and raffinate stream 570*c*, which is enriched in isobutene and produced by treating bottoms stream 530*b* (which is formed by distillation unit 530) with an additional butadiene removal unit 570. The MTBE that is produced by MTBE synthesis unit 580 is recovered as product stream 580*a*, while other components, such as 1-butene and 2-butenes, are recovered as raffinate stream 580*b*. FIG. 5 also shows that butadiene removal unit 570 produces butadiene stream 570*b*, as well as raffinate stream 570*a*.

Figure 6:
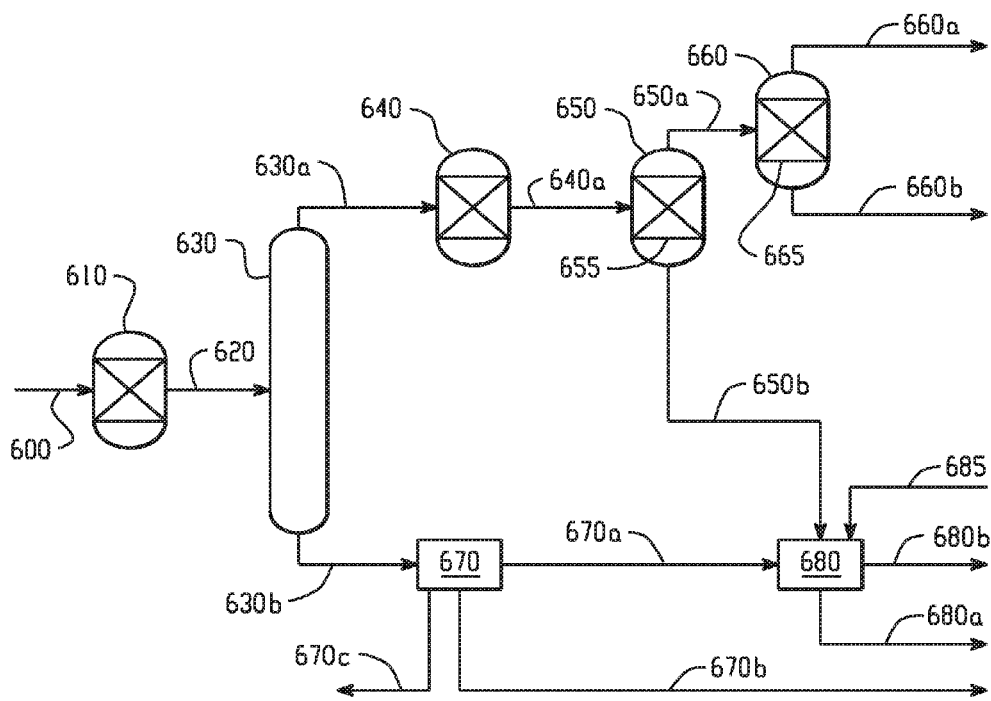
FIG. 6 is a schematic diagram depicting a method for C4 purification for MTBE synthesis in accordance with another exemplary implementation of the present disclosure.

FIG. 6 schematically depicts an exemplary method and system for separating and purifying a C4 stream according to yet another implementation of the invention. Distillate 630*a*, which is produced by distillation unit 630, has a relatively low concentration of butadiene impurities. To further reduce the concentration of butadiene impurities, distillate 630*a* is sent to selective hydrogenation unit 640. Product stream 640*a* from selective hydrogenation unit 640 is then used as an input stream for separation unit 650, which comprises molecular sieves 655. Preferably, the molecular sieves 655 have a pore size of 3 Å, 4 Å, 5 Å, or 10 Å (13×), although this invention expressly contemplates others as well. Separation unit 650 produces raffinate stream 650*a* comprising a mixture of 1-butene and 2-butenes. Raffinate stream 650*a* serves as an input stream for separation unit 660, which comprises molecular sieves 665. In certain exemplary implementations, the molecular sieves 665 are molecular sieves with 3 Å, 4 Å, 5 Å, or 10 Å (13×) pore sizes. Separation unit 660 produces 1-butene stream 660*a* and 2-butenes stream 660*b*. In preferred embodiments, the concentration of 1-butene in stream 660*a* is 95 wt. %, more preferably 97 wt. %, and even more preferably 99 wt. %. Product stream 650*b*, which comprises isobutene, can be directly used as an input stream for MTBE synthesis unit 680. FIG. 6 shows two other input streams into MTBE synthesis unit 680, namely methanol stream 685 and raffinate stream 670*c*, which is enriched in isobutene and produced by treating bottoms stream 630*b* (formed by distillation unit 630) with an additional butadiene removal unit 670. The MTBE that is produced by MTBE synthesis unit 680 is recovered as product stream 680*a*, while other components, such as 1-butene and 2-butenes, are recovered as raffinate stream 680*b*. FIG. 6 also shows that butadiene removal unit 670 produces butadiene stream 670*b*, as well as raffinate stream 670*c*, both of which can be subjected to further downstream processing.

Figure 7:
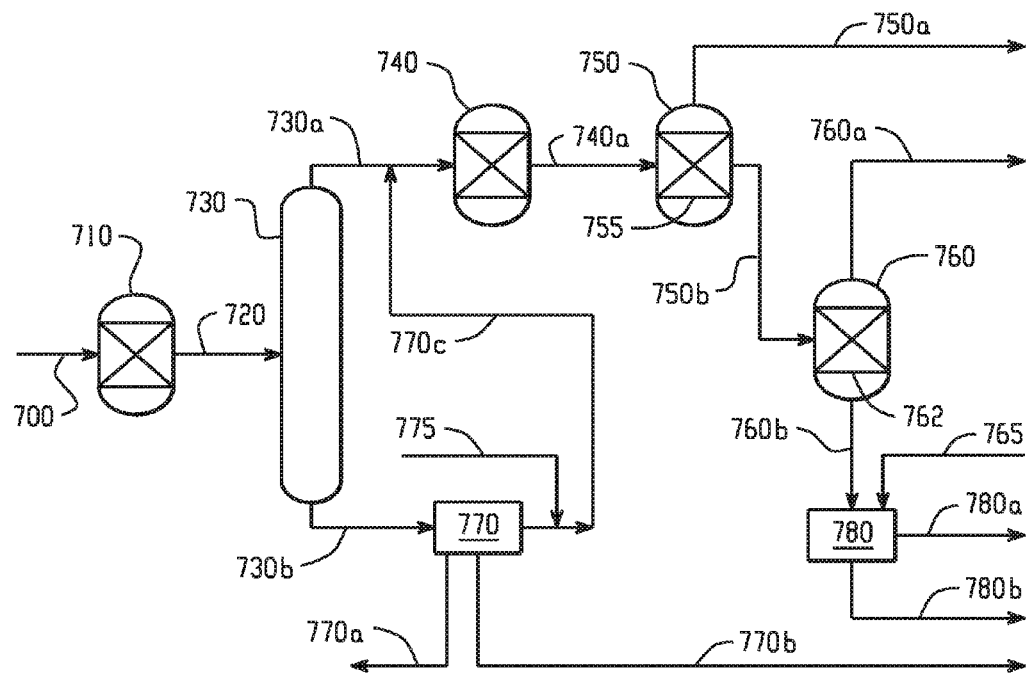
FIG. 7 is schematic diagram depicting a method of producing MTBE according to another embodiment of the present disclosure.

FIG. 7 schematically depicts an exemplary method and system for separating and purifying a C4 stream according to yet another implementation of the invention. Distillate 730*a* from distillation unit 730 is combined with product stream 770*c*, which is produced by further treating product stream 730*b* from distillation unit 730 with a butadiene removal step in butadiene removal unit 770. Optionally, product stream 770*c* can also comprise hydrocarbons from external raffinate stream 775 as indicated in FIG. 7.

The combined product streams 730*a* and 770*c* are selectively hydrogenated in selective hydrogenation unit 740 to form product stream 740*a*. As shown in FIG. 7, product stream 740*a* is an input stream for 1-butene separation unit 750, which comprises molecular sieves that separate 1-butene from the remaining species to produce 1-butene stream 750*a* and iC4 stream 750*b*. Preferably, the molecular sieves 755 present in separation unit 750 are chosen such that product stream 750*a* comprises 1-butene at a concentration of greater than 90 wt. %. For example, the concentration of 1-butene in product stream 750*a* can be at least 95%, and in certain embodiments is 96, 97, 98, or 99 wt. %. Non-limiting examples of suitable molecular sieves include molecular sieves with 3 Å, 4 Å, 5 Å, or 10 Å (13×) pore sizes, although this invention expressly contemplates others as well. If desired, product stream 750*b* containing iC4s can be further purified by an additional iC4 separation unit, identified by reference numeral 760 in FIG. 7. Separation unit 760 comprises molecular sieves 762. When iC4 separation unit is present, it produces purified iC4 stream 760b and raffinate stream 760a. Purified iC4 stream 760b can be used as an input stream for MTBE synthesis unit 780. FIG. 7 shows one other input stream into MTBE synthesis unit 780, namely methanol stream 765. The MTBE that is produced by MTBE synthesis unit 780 is recovered as product stream 780b, while other components, such as 1-butene and 2-butenes, are recovered as raffinate stream 780a. FIG. 7 also shows that butadiene removal unit 770 produces butadiene stream 770b, as well as raffinate stream 770a, both of which can be subjected to further downstream processing.

Figure 8:
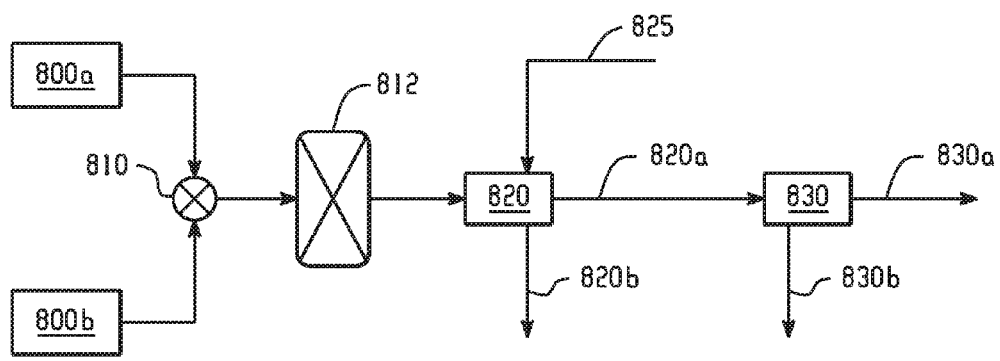
FIG. 8 is schematic diagram depicting a method of producing MTBE according to another embodiment of the present disclosure.

FIG. 8 schematically depicts an exemplary method and system for according to yet another implementation of the invention. In FIG. 8, olefin sources 800a and 800b are fluidly connected to a valve 812 that admits the olefins from source 800a and/or 800b into selective hydrogenation unit 812, which selectively hydrogenates acetylinic impurities present in the olefin streams. The output from selective hydrogenation unit 812 is then sent to MTBE synthesis unit 820, where it reacts with a methanol stream 825 to produce MTBE stream 820b and olefin stream 820a. Olefin stream 820a is further purified by treatment in butadiene separation unit 830 to produce butadiene stream 830a and raffinate stream 830b.

Figure 9:
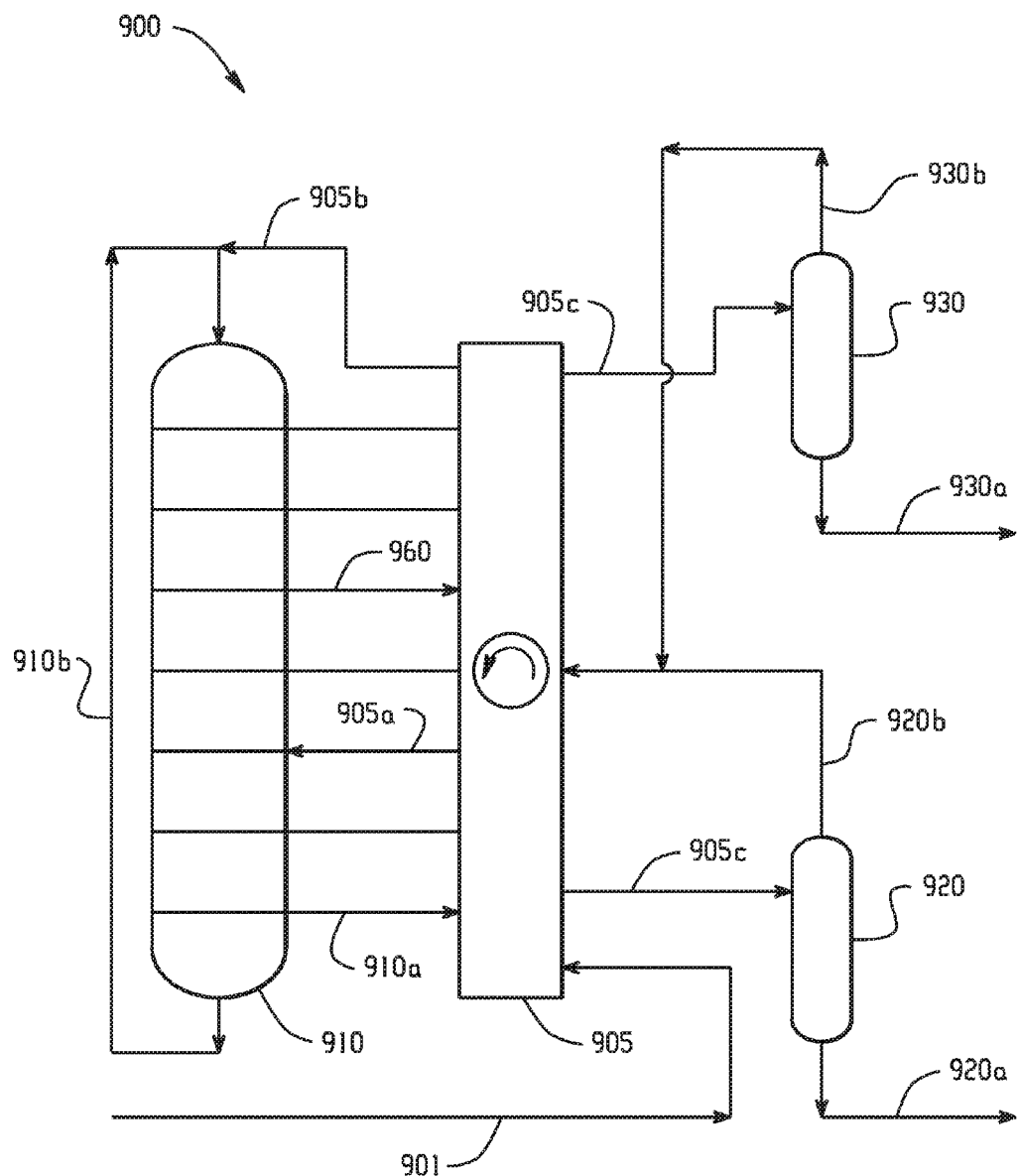
FIG. 9 is a schematic diagram of an exemplary C4 separation system for use in the methods and systems of the present disclosure.

FIG. 9 shows a schematic diagram of a separation unit 900 suitable for use with the methods and systems of the invention. In FIG. 9, input C4 stream 901 is directed to manifold 905, which is fluidly connected with solid adsorbent chamber 910. Chamber 910 contains a solid adsorbent capable of causing separation of at least two C4 species in input C4 stream 901. The solid adsorbent can be, for example, molecular sieves as described herein. As the skilled artisan will appreciate, the specific type of molecular sieves actually used will depend on the product streams desired and the purities of such product streams. In certain embodiments, the invention contemplates using molecular sieves with 3 Å, 4 Å, 5 Å, or 10 Å (13×) pore sizes as solid adsorbents for producing a highly purified 1-butene from a mixed C4 stream, with a purity of 95 wt. %, more preferably 97 wt. %, and even more preferably 99 wt. %. In addition, the invention contemplates using molecular sieves with pore sizes of 3 Å, 4 Å, 5 Å, or 10 Å as solid adsorbents for separating iC4s, particularly isobutene from a mixed C4 stream. The purity of the isobutene streams is preferably at least 50 wt. %, more preferably 60 wt. %, even more preferably 70 wt. %, or 80 wt. %, or 90 wt. %. If desired, the solid adsorbents can be selected to separate 2-butenes from a mixed C4 stream. Suitable solid adsorbents for achieving this separation include molecular sieves with a pore size of 3 Å, 4 Å, 5 Å, or 10 Å (13×), although other types are expressly contemplated by the invention.

The fluid connections between manifold 905 and solid adsorbent chamber 910 include a connection for feed streams 905a and 905b, a connection for product extract stream 960, and a connection for raffinate stream 910a. Note that solid adsorbent chamber 910 is equipped with connections for recirculating stream 910b. FIG. 9 also shows that product extract stream 960 passes through fluid connection 905c to extract column 930, which further separates the product extract stream 960 to produce a product stream 930a and a recycled stream 930b that is directed back to the manifold 905 for further processing. Raffinate stream 910a is directed to raffinate column 920, which further separates raffinate stream 910a into product stream 920a and recycle stream 920b. In preferred embodiments, raffinate stream 920a comprises isobutene and is used as an input stream for either a further separation unit or an MTBE synthesis unit.

The methods of producing methyl tertiary-butyl ether (MTBE) disclosed herein include(s) at least the following embodiments:

Embodiment 1

A method of producing methyl tertiary-butyl ether (MTBE), comprising: selectively hydrogenating a crude C4 stream to remove acetylinic impurities contained therein; distilling the hydrogenated crude C4 stream to remove butadiene impurities contained in the hydrogenated crude C4 stream, forming a distillate stream and a bottoms stream; exposing the distillate to a separation unit comprising a solid adsorbent to produce a first product stream comprising 1-butene and a second product stream comprising isobutene; reacting the second product stream with a methanol stream to produce methyl tertiary-butyl ether.

Embodiment 2

The method according to Embodiment 1, further comprising processing the bottoms stream to remove butadiene impurities, forming a third product stream and reacting the third product stream with the methanol stream to produce methyl tertiary-butyl ether.

Embodiment 3

The method according to Embodiment 1 or Embodiment 2, wherein the method further comprises selectively hydrogenating the distillate to substantially reduce the butadiene concentration prior to exposing the distillate to the separation unit.

Embodiment 4

The method according to any of Embodiments 1-3, wherein selectively hydrogenating the crude C4 stream reduces the concentration of the acetylinic impurities to less than 100 parts per million.

Embodiment 5

The method according to any of Embodiments 1-4, wherein the concentration of 1-butene in the first product stream is approximately 99 wt. %.

Embodiment 6

A method of producing methyl tertiary-butyl ether (MTBE), comprising: selectively hydrogenating a crude C4 stream to remove acetylinic impurities contained therein; distilling the hydrogenated crude C4 stream in a distillation unit to remove butadiene impurities contained in the hydrogenated crude C4 stream, forming a distillate stream and a bottoms stream; choosing a separation unit from either a first separation unit or a second separation unit, wherein the first separation unit and second separation unit are fluidly connected to the distillation unit and arranged in parallel; wherein the first separation unit comprises a first solid adsorbent capable of causing separation of the distillate stream into a first product stream comprising 1-butene and a first raffinate stream; and wherein the second separation unit comprises a second solid adsorbent different from the first solid adsorbent, the second solid adsorbent capable of causing separation of the distillate stream into a second product stream comprising a mixture of isobutene and isobutane and a second raffinate stream; exposing the distillate to the chosen separation unit to cause separation of the distillate such that, when the first separation unit is chosen, the first raffinate stream is reacted with a methanol stream to form methyl tertiary-butyl ether; and when the second separation unit is chosen, the second product stream is reacted with a methanol stream to form methyl tertiary-butyl ether.

Embodiment 7

The method according to Embodiment 6, further comprising processing the bottoms stream to remove butadiene impurities, thereby forming a third product stream and reacting the third product stream with the methanol stream to produce methyl tertiary-butyl ether.

Embodiment 8

A method of producing methyl tertiary-butyl ether, comprising: selectively hydrogenating a crude C4 stream to remove acetylinic impurities contained therein; distilling the hydrogenated crude C4 stream to remove butadiene impurities contained in the hydrogenated crude C4 stream, thereby forming a distillate stream and a bottoms stream; selectively hydrogenating the distillate stream to further reduce the concentration of butadiene impurities to form a first product stream; exposing the first product stream to a first separation unit comprising a solid adsorbent to produce a second product stream comprising 1-butene and a third product stream comprising a mixture of isobutene and isobutane; exposing the third product stream to a second separation unit comprising a solid adsorbent to produce a fourth product stream comprising a mixture of isobutene and isobutane and a fifth product stream enriched in 2-butenes; and reacting the fourth product stream with a methanol stream to produce methyl tertiary-butyl ether.

Embodiment 9

The method according to Embodiment 8, further comprising processing the bottoms stream to remove butadiene impurities, thereby forming a sixth product stream and reacting the sixth product stream with the methanol stream to produce methyl tertiary-butyl ether.

Embodiment 10

A method of producing methyl tertiary-butyl ether, comprising: selectively hydrogenating a crude C4 stream to remove acetylinic impurities contained therein; distilling the hydrogenated crude C4 stream to remove butadiene impurities contained in the hydrogenated crude C4 stream, thereby forming a distillate stream and a bottoms stream; selectively hydrogenating the distillate stream to further reduce the concentration of butadiene impurities to form a first product stream; exposing the first product stream to a first separation unit comprising a solid adsorbent to produce a second product stream comprising 1-butene and a third product stream comprising a mixture of isobutene and isobutane; exposing the second product stream to a second separation unit comprising a solid adsorbent to produce a fourth product stream comprising 1-butene and a fifth product stream comprising 2-butenes; and reacting the third product stream with a methanol stream to produce methyl tertiary-butyl ether.

Embodiment 11

The method according to Embodiment 10, further comprising processing the bottoms stream to remove butadiene impurities, thereby forming a sixth product stream and reacting the sixth product stream with the methanol stream to produce methyl tertiary-butyl ether.

Embodiment 12

A method of producing methyl tertiary-butyl ether, comprising: selectively hydrogenating a crude C4 stream to remove acetylinic impurities contained therein; distilling the hydrogenated crude C4 stream to remove butadiene impurities contained in the hydrogenated crude C4 stream, thereby forming a distillate stream and a bottoms stream; selectively hydrogenating the distillate stream to further reduce the concentration of butadiene impurities to form a first product stream; exposing the first product stream to a first separation unit comprising a solid adsorbent to produce a second product stream comprising 1-butene and a third product stream comprising a mixture of isobutene and isobutane; optionally exposing the third product stream a second separation unit to produce a fourth product stream comprising 2-butene and a fifth product stream comprising isobutene; reacting the fifth product stream with a methanol stream to produce methyl tertiary-butyl ether.

Embodiment 13

The method according to Embodiment 12, further comprising processing the bottoms stream to remove butadiene impurities, thereby forming a sixth product stream and combining the sixth product stream with the distillate stream.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

We claim:

1. A method of producing methyl tertiary-butyl ether, comprising:
   selectively hydrogenating a crude C4 stream to remove acetylinic impurities contained therein;
   distilling the hydrogenated crude C4 stream to remove butadiene impurities contained in the hydrogenated crude C4 stream, forming a distillate stream and a bottoms stream;
   exposing the distillate to a separation unit comprising a solid adsorbent to produce a first product stream comprising 1-butene and a second product stream comprising isobutene;
   reacting the second product stream with a methanol stream to produce methyl tertiary-butyl ether.

2. The method according to claim 1, further comprising processing the bottoms stream to remove butadiene impurities, forming a third product stream and reacting the third product stream with the methanol stream to produce methyl tertiary-butyl ether.

3. The method according to claim 1, wherein the method further comprises selectively hydrogenating the distillate to substantially reduce the butadiene concentration prior to exposing the distillate to the separation unit.

4. The method according to claim 1, wherein selectively hydrogenating the crude C4 stream reduces the concentration of the acetylinic impurities to less than 100 parts per million.

5. The method according to claim 1, wherein the concentration of 1-butene in the first product stream is approximately 99 wt. %.

6. The method of claim 1, further comprising:
   choosing a separation unit from either a first separation unit or a second separation unit,
   wherein the first separation unit and second separation unit are fluidly connected to the distillation unit and arranged in parallel;
   wherein the first separation unit comprises a first solid adsorbent capable of causing separation of the distillate stream into a first product stream comprising 1-butene and a first raffinate stream; and
   wherein the second separation unit comprises a second solid adsorbent different from the first solid adsorbent, the second solid adsorbent capable of causing separation of the distillate stream into a second product stream comprising a mixture of isobutene and isobutane and a second raffinate stream;
   exposing the distillate to the chosen separation unit to cause separation of the distillate such that,
   when the first separation unit is chosen, the first raffinate stream is reacted with a methanol stream to form methyl tertiary-butyl ether; and
   when the second separation unit is chosen, the second product stream is reacted with a methanol stream to form methyl tertiary-butyl ether.

7. The method according to claim 6, further comprising processing the bottoms stream to remove butadiene impurities, thereby forming a third product stream and reacting the third product stream with the methanol stream to produce methyl tertiary-butyl ether.

8. A method of producing methyl tertiary-butyl ether, comprising:
   selectively hydrogenating a crude C4 stream to remove acetylinic impurities contained therein;
   distilling the hydrogenated crude C4 stream to remove butadiene impurities contained in the hydrogenated crude C4 stream, thereby forming a distillate stream and a bottoms stream;
   selectively hydrogenating the distillate stream to further reduce the concentration of butadiene impurities to form a first product stream;
   exposing the first product stream to a first separation unit comprising a solid adsorbent to produce a second product stream comprising 1-butene and a third product stream comprising a mixture of isobutene and isobutane;
   exposing the third product stream to a second separation unit comprising a solid adsorbent to produce a fourth product stream comprising a mixture of isobutene and isobutane and a fifth product stream enriched in 2-butenes; and
   reacting the fourth product stream with a methanol stream to produce methyl tertiary-butyl ether.

9. The method according to claim 8, further comprising processing the bottoms stream to remove butadiene impurities, thereby forming a sixth product stream and reacting the sixth product stream with the methanol stream to produce methyl tertiary-butyl ether.

10. The method of claim 1 further comprising:
selectively hydrogenating the distillate stream to further reduce the concentration of butadiene impurities to form a first product stream;
exposing the first product stream to a first separation unit comprising a solid adsorbent to produce a second product stream comprising 1-butene and a third product stream comprising a mixture of isobutene and isobutane;
exposing the second product stream to a second separation unit comprising a solid adsorbent to produce a fourth product stream comprising 1-butene and a fifth product stream comprising 2-butenes; and
reacting the third product stream with a methanol stream to produce methyl tertiary-butyl ether.

11. The method according to claim 10, further comprising processing the bottoms stream to remove butadiene impurities, thereby forming a sixth product stream and reacting the sixth product stream with the methanol stream to produce methyl tertiary-butyl ether.

12. A method of producing methyl tertiary-butyl ether, comprising:
selectively hydrogenating a crude C4 stream to remove acetylinic impurities contained therein;
distilling the hydrogenated crude C4 stream to remove butadiene impurities contained in the hydrogenated crude C4 stream, thereby forming a distillate stream and a bottoms stream;
selectively hydrogenating the distillate stream to further reduce the concentration of butadiene impurities to form a first product stream;
exposing the first product stream to a first separation unit comprising a solid adsorbent to produce a second product stream comprising 1-butene and a third product stream comprising a mixture of isobutene and isobutane;
optionally exposing the third product stream to a second separation unit to produce a fourth product stream comprising 2-butene and a fifth product stream comprising isobutene;
reacting the fifth product stream with a methanol stream to produce methyl tertiary-butyl ether.

13. The method according to claim 12, further comprising processing the bottoms stream to remove butadiene impurities, thereby forming a sixth product stream and combining the sixth product stream with the distillate stream.

* * * * *